(12) United States Patent
Nguyen et al.

(10) Patent No.: US 8,469,924 B2
(45) Date of Patent: Jun. 25, 2013

(54) METHOD AND APPARATUS FOR GENERATING VASCULAR TREATMENT FOAM

(75) Inventors: Hoa D. Nguyen, San Jose, CA (US); Michael S. Mirizzi, San Jose, CA (US)

(73) Assignee: Covidien LP, Mansfield, MA (US)

( * ) Notice: Subject to any disclaimer, the term of this patent is extended or adjusted under 35 U.S.C. 154(b) by 1214 days.

(21) Appl. No.: 11/696,696

(22) Filed: Apr. 4, 2007

(65) Prior Publication Data

US 2007/0244429 A1  Oct. 18, 2007

Related U.S. Application Data

(60) Provisional application No. 60/744,267, filed on Apr. 4, 2006.

(51) Int. Cl.
*A61M 37/00* (2006.01)
(52) U.S. Cl.
USPC .............................................. 604/89; 604/82
(58) Field of Classification Search
USPC .................. 604/57, 82, 89, 181, 187, 278
See application file for complete search history.

(56) References Cited

U.S. PATENT DOCUMENTS

| 2,498,393 A | 2/1950 | Clewell |
| 3,376,999 A | 4/1968 | De Hart et al. |
| 3,471,064 A | 10/1969 | Micallef |
| 5,205,647 A | 4/1993 | Ricciardi |
| 5,352,036 A | 10/1994 | Haber et al. |
| 5,676,962 A | 10/1997 | Cabrera Garrido et al. |
| 5,899,881 A * | 5/1999 | Grimard et al. ................ 604/89 |
| 6,575,930 B1 | 6/2003 | Trombley, III et al. |
| 2002/0041537 A1 | 4/2002 | Yale |
| 2003/0185096 A1 | 10/2003 | Hollstein et al. |
| 2005/0105385 A1 | 5/2005 | McGill et al. |
| 2005/0238540 A1 | 10/2005 | Swon et al. |
| 2007/0104651 A1 | 5/2007 | Wright et al. |

FOREIGN PATENT DOCUMENTS

| DE | 30 43 335 A1 | 6/1982 |
| DE | 44 19 279 C1 | 9/1995 |
| GB | 2 369 996 B | 6/2002 |
| WO | WO 00/34663 A | 6/2000 |

OTHER PUBLICATIONS

International Search Report and Written Opinion for Application No. PCT-US2007-008452 mailed Feb. 13, 2008.
Alessandro Frullini, MD, FACP; New Technique in Producing Sclerosing Foam in a Disposable Syringe; Florence, Italy.
Alessandro Frullini; Foam Sclerotherapy:A Review; Studio Flebologico Incisa Valarno, Florence, Italy.
Michael P. Goldman, MD, Robert A. Weiss, MD, John J. Bergan, MD; Journal of the American Academy of Dermatology—Continuing Medical Education—Diagnosis and treatment of varicose veins.

(Continued)

*Primary Examiner* — Victoria P Shumate
(74) *Attorney, Agent, or Firm* — Thomas M. Johnston, Esq.

(57) ABSTRACT

Apparatus and methods for generating foam are disclosed. The inventions can be used for generating foam for sclerotherapy. A foaming element can be agitated within a foaming chamber by a drive unit that does not touch the foaming element, but actuates it from outside the foaming chamber. The foaming element and drive unit can be magnetically coupled. A syringe can be used to form a foaming chamber.

15 Claims, 10 Drawing Sheets

OTHER PUBLICATIONS

Lorenzo Tessari, MD, Attilio Cavezzi, MD, Alessandro Frullini, MD, FACP; Preliminary Experience with a New Sclerosing Foam in the Treatment of Varicose Veins; Glauco Bassi Foundation, Trieste, Italy, Vascular Unit, Stell Maris Clinic, S. Benedetto del Tronto, Italy and Studio Flebologico, Incisa Valarno, Florence, Italy.

* cited by examiner

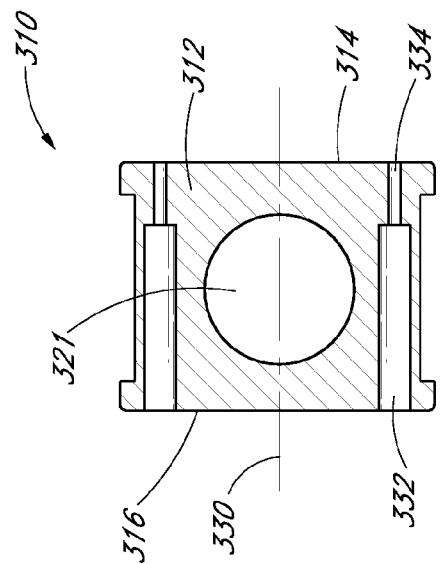
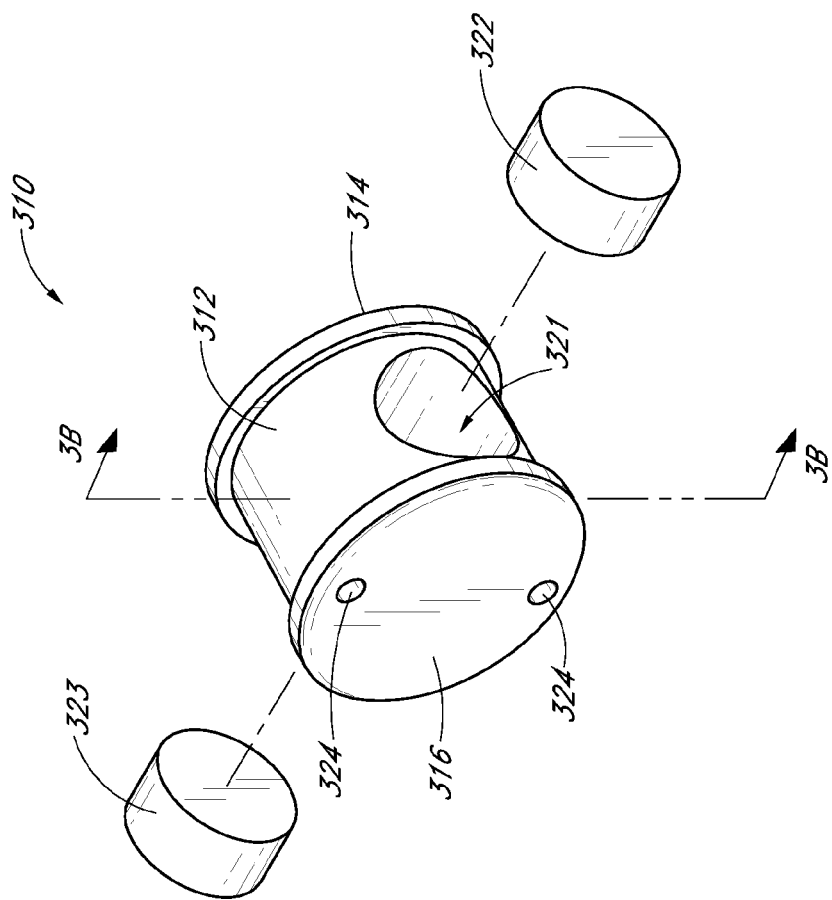
FIG. 3B
FIG. 3A

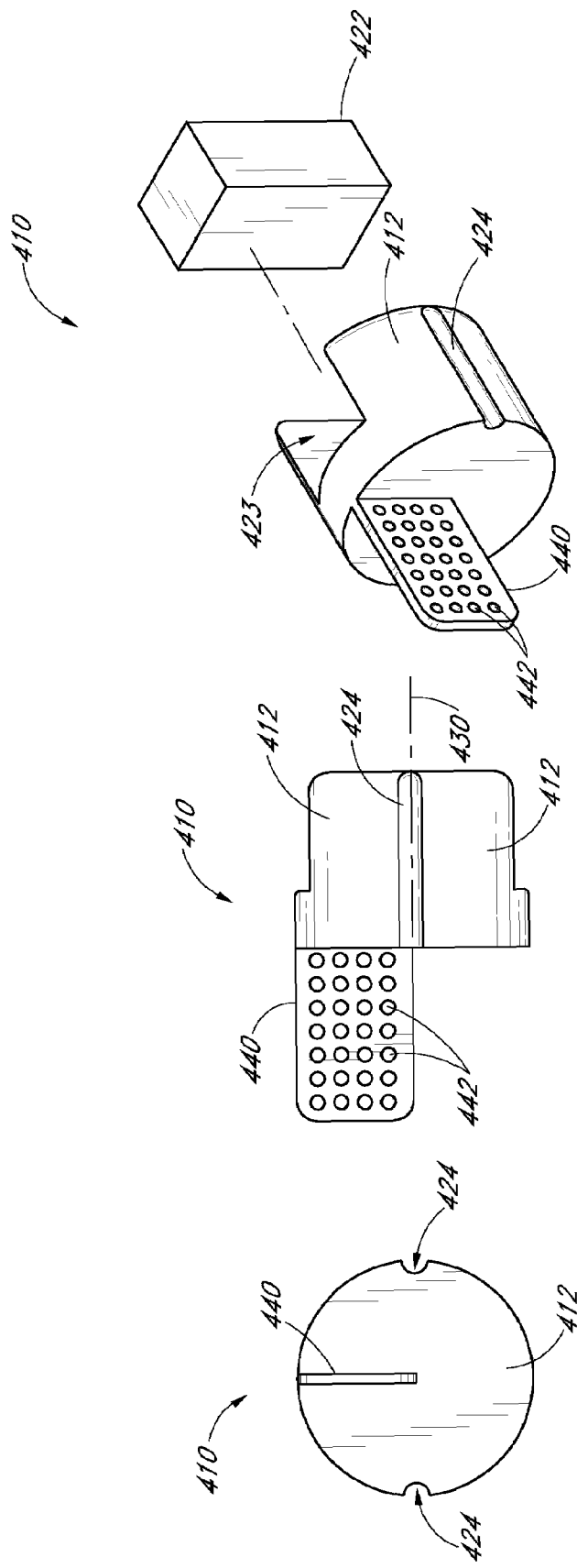

METHOD AND APPARATUS FOR GENERATING VASCULAR TREATMENT FOAM

CROSS-REFERENCE TO RELATED APPLICATIONS

This application claims priority to U.S. Provisional Patent Application No. 60/744,267, filed Apr. 4, 2006, titled SCLEROTBERAPY FOAM GENERATORS, which is hereby incorporated by reference in its entirety and made part of this specification.

BACKGROUND

1. Field

Certain embodiments disclosed herein relate to apparatus and methods for preparing a foamed vascular treatment agent, such as a foamed sclerosant.

2. Description of the Related Art

Sclerotherapy is a treatment of varicose veins by injecting sclerosing solution into the veins to cause sclerosis. When the liquid sclerosing solution is injected into the vein, it is mixed with the blood contained in the vein and is diluted in an unknown proportion. The results can be uncertain and unpredictable. However, when sclerosing foam is used (instead of a more flowing liquid), the results are more predictable. Sclerosing foams can displace the blood inside the vessels and have fuller contact with the vein inner wall. Low doses and low concentrations of drugs may be successfully employed because the foam resists dilution. Various foam generation techniques in the art have proven cumbersome and difficult to automate. The disclosed inventions solve many of these problems.

SUMMARY OF THE INVENTION

Embodiments described herein have several features, no single one of which is solely responsible for their desirable attributes. Without limiting the scope of the invention as expressed by the claims, some of the advantageous features will now be discussed briefly.

In some embodiments, there is provided an apparatus for preparing foamed vascular treatment fluid. The apparatus can comprise: a foaming chamber; a vascular treatment fluid in the chamber; and a foaming element in the chamber, the foaming element being moveable within the chamber and in the fluid. The foaming element can have one or more flow passages therein so that movement of the foaming element in the vascular treatment fluid tends to force the fluid through the one or more flow passages. In some embodiments, the chamber in the apparatus can comprise a syringe barrel. In some embodiments, the apparatus can further comprise a drive unit located outside the chamber, the drive unit being configured to drivingly couple to the foaming element without a drive shaft or other linkage extending into the chamber. In an embodiment having such a drive unit, the drive unit can further be configured to magnetically couple to said foaming element. In another embodiment having such a drive unit, the drive unit can alternatively be configured to electrostatically couple to said foaming element. In some embodiments, the vascular treatment fluid can comprise a sclerosant. In some embodiments, the foaming element of the apparatus is magnetic, and the apparatus further comprises a magnetic drive unit configured to magnetically engage the foaming element. In an embodiment having such a magnetic drive unit, the magnetic drive unit can be housed in a base which is configured to removably receive the foaming chamber. In an embodiment with a magnetic drive unit housed in this way with a base thus configured, the chamber can be located in a syringe and the base can form a receptacle which is configured to removably receive the syringe. In an embodiment with the chamber thus located and the base forming a receptacle thus configured, the magnetic drive unit can be configured to magnetically engage the foaming element upon placement of the syringe in the receptacle.

In some embodiments, there is provided a method of preparing vascular treatment agent. The method comprises contactlessly moving an agitator within a volume of vascular treatment agent disposed within a chamber. In some embodiments, the method further comprises foaming the vascular treatment agent via moving the agitator. In embodiments where the agent is foamed in this way, the method can further comprise injecting said foamed vascular treatment agent into a blood vessel of a patient. In such methods, the agent can comprise a sclerosant. In such methods, the blood vessel can comprise a vein. In methods that include the steps described above, (including foaming the agent via moving the agitator), the method can further comprise reducing patency of the blood vessel with the vascular treatment agent. In embodiments of the method that comprise contactlessly moving an agitator within a volume of vascular treatment agent disposed within a chamber, moving the agitator can comprise linearly moving said agitator. In embodiments where the agitator is moved thus, the chamber can have a longitudinal axis, and linearly moving the agitator can comprise linearly reciprocating the agitator along the longitudinal axis. In embodiments of the method that comprise contactlessly moving an agitator within a volume of vascular treatment agent disposed within a chamber, moving said agitator can comprise rotating said agitator. In embodiments where the agitator is moved thus, the chamber can have a longitudinal axis, and rotating the agitator can comprise rotating the agitator about the longitudinal axis. In embodiments of the method that comprise contactlessly moving an agitator within a volume of vascular treatment agent disposed within a chamber, contactlessly moving the agitator can comprise magnetically moving the agitator. In embodiments of the method that comprise contactlessly moving an agitator within a volume of vascular treatment agent disposed within a chamber, contactlessly moving the agitator can comprise electrostatically moving the agitator. In embodiments of the method that comprise contactlessly moving an agitator within a volume of vascular treatment agent disposed within a chamber, contactlessly moving the agitator can comprise inertially moving the agitator. In embodiments of the method that comprise contactlessly moving an agitator within a volume of vascular treatment agent disposed within a chamber, the agitator can comprise a member having one or more flow passages therein, and moving the agitator can comprise forcing at least a portion of the vascular treatment agent through the one or more flow passages. In embodiments of the method that comprise contactlessly moving an agitator within a volume of vascular treatment agent disposed within a chamber, the chamber can comprise a syringe. In such methods where the chamber comprises a syringe, the agitator can be magnetically coupled to a magnetic drive unit, and contactlessly moving the agitator within the chamber can comprise contactlessly moving the agitator within the syringe with the drive unit. In such an embodiment, the method can further comprise receiving the syringe in the drive unit.

In some embodiments, there is provided an apparatus for preparing a vascular treatment agent. The apparatus can comprise: a drive unit; and an impeller that comprises a generally solid member having one or more passages extending therethrough, the impeller being contactlessly and drivingly coupled to the drive unit. In some embodiments, the impeller of the apparatus can comprise a generally cylindrical body having a first end surface and an opposing second end surface, and the one or more passages can extend through the body from the first surface to the second surface. In embodiments with passages extending in this way, one or more passages can have a diameter of 0.010 inch to 0.030 inch. In embodiments with passages extending through the body from the first surface to the second surface, at least one of the one or more passages can comprise a larger-diameter portion and a smaller-diameter portion abutting said larger-diameter portion in end-to-end fashion. In embodiments with an impeller comprising a generally cylindrical body having a first end surface and an opposing second end surface, also having one or more passages extending through the body from the first surface to the second surface, the impeller can have a longitudinal axis passing through the first and second end surfaces, and the one or more passages can extend generally parallel to the longitudinal axis. In embodiments with an impeller comprising a generally cylindrical body having a first end surface and an opposing second end surface, also having one or more passages extending through the body from the first surface to the second surface, the apparatus can further comprise a chamber containing a volume of vascular treatment agent, the volume having a longitudinal axis, wherein the impeller is moveable linearly in the chamber along the longitudinal axis of the chamber. In such an apparatus comprising such a chamber, the chamber can be located in a syringe. In embodiments with an impeller comprising a generally cylindrical body having a first end surface and an opposing second end surface, also having one or more passages extending through the body from the first surface to the second surface, the drive unit can comprise a magnetic drive and the impeller can comprise a magnet connected to or disposed in the body. In some embodiments of an apparatus for preparing a vascular treatment agent comprising a drive unit and an impeller that comprises a generally solid member having one or more passages extending therethrough, the impeller being contactlessly and drivingly coupled to the drive unit, the impeller can comprise a generally cylindrical body and a paddle extending from the body, and one or more passages can extend through the paddle. In such embodiments, the body can have a longitudinal axis and the paddle can extend from an end of the body and along the longitudinal axis. In such embodiments, the paddle can extend along substantially the entire width of the end of the body. Alternatively, however, in such embodiments having a body with a longitudinal axis and where the paddle extends from an end of the body and along the longitudinal axis, the paddle can extend along about half the width of the end of the body. In embodiments of an apparatus for preparing a vascular treatment agent that comprise a drive unit and an impeller that comprises a generally solid member having one or more passages extending therethrough, the impeller being contactlessly and drivingly coupled to the drive unit, the impeller further comprising a generally cylindrical body and a paddle extending from the body, where one or more passages extend through the paddle, the one or more passages can have a diameter of 0.010 inch to 0.060 inch. In embodiments of an apparatus for preparing a vascular treatment agent that comprise a drive unit and an impeller that comprises a generally solid member having one or more passages extending therethrough, the impeller being contactlessly and drivingly coupled to the drive unit, the impeller further comprising a generally cylindrical body and a paddle extending from the body, where one or more passages extend through the paddle, the apparatus can further comprise a chamber containing a volume of vascular treatment agent, the volume having a longitudinal axis, wherein the paddle is rotatable in the chamber about the longitudinal axis of the chamber. In such an embodiment, the chamber can be located in a syringe. In embodiments of an apparatus for preparing a vascular treatment agent that comprise a drive unit and an impeller that comprises a generally solid member having one or more passages extending therethrough, the impeller being contactlessly and drivingly coupled to the drive unit, the impeller further comprising a generally cylindrical body and a paddle extending from the body, where one or more passages extend through the paddle, the drive unit can comprise a magnetic drive and the impeller can comprise a magnet connected to or disposed in the body. In embodiments of an apparatus for preparing a vascular treatment agent comprising a drive unit and an impeller that comprises a generally solid member having one or more passages extending therethrough, the impeller being contactlessly and drivingly coupled to the drive unit, the impeller can comprise a generally cylindrical body and a plurality of elongate protrusions extending from the body. In such an embodiment, the impeller elements can be spaced apart from each other by a substantially uniform distance. In such an embodiment, the impeller elements can be arranged in a generally circular pattern on an end surface of the body.

In some embodiments, there is provided an apparatus for preparing a vascular treatment agent. The apparatus can comprise: a syringe, the syringe having an internal chamber containing a vascular treatment fluid; an impeller located in the chamber; a drive system located entirely outside the chamber, the drive system being contactlessly and drivingly coupled to the impeller; the impeller comprising a generally solid member having one or more fluid flow passages extending therethrough, such that movement of the impeller in the treatment fluid tends to force the treatment fluid through the fluid flow passages. In such an apparatus, the drive system can be magnetically coupled to the impeller. In such an embodiment, the impeller can comprise a magnet and the drive system can comprise a magnetic drive. In embodiments of an apparatus for preparing a vascular treatment agent comprising: a syringe, the syringe having an internal chamber containing a vascular treatment fluid; an impeller located in the chamber; a drive system located entirely outside the chamber, the drive system being contactlessly and drivingly coupled to the impeller; the impeller comprising a generally solid member having one or more fluid flow passages extending therethrough, such that movement of the impeller in the treatment fluid tends to force the treatment fluid through the fluid flow passages, the drive system can be magnetically coupled to the impeller. In embodiments of an apparatus for preparing a vascular treatment agent comprising: a syringe, the syringe having an internal chamber containing a vascular treatment fluid; an impeller located in the chamber; a drive system located entirely outside the chamber, the drive system being contactlessly and drivingly coupled to the impeller; the impeller comprising a generally solid member having one or more fluid flow passages extending therethrough, such that movement of the impeller in the treatment fluid tends to force the treatment fluid through the fluid flow passages, the vascular treatment fluid can comprise a sclerosant. In embodiments of an apparatus for preparing a vascular treatment agent comprising: a syringe, the syringe having an internal chamber containing a vascular treatment fluid; an impeller located in the chamber; a drive system located entirely outside the chamber, the drive system being contactlessly and drivingly coupled to the impeller; the impeller comprising a generally solid member having one or more fluid flow passages extending therethrough, such that movement of the impeller in the treatment fluid tends to force the treatment fluid through the fluid flow passages, the fluid flow passages can have at least a portion with a diameter of 0.010 inch to 0.060 inch. In embodiments of an apparatus for preparing a vascular treatment agent comprising: a syringe, the syringe having an internal chamber containing a vascular treatment fluid; an impeller located in the chamber; a drive system located entirely outside the chamber, the drive system being contactlessly and drivingly coupled to the impeller; the impeller comprising a generally solid member having one or more fluid flow passages extending therethrough, such that movement of the impeller in the treatment fluid tends to force the treatment fluid through the fluid flow passages, the drive system can be housed in a base which is configured to removably receive the syringe.

In some embodiments, there is provided a method of vascular therapy comprising: creating a foamed vascular treatment fluid by contactlessly agitating a volume of the treatment fluid located in a barrel of a syringe; and injecting the foamed treatment fluid into a blood vessel of a patient with the syringe. In such a method, the vascular treatment fluid can comprise a sclerosant. In such a method having such a treatment fluid, the blood vessel can comprise a vein. In such a method having such a blood vessel, the blood vessel can comprise a varicose vein. In embodiments of a method of vascular therapy that comprise: creating a foamed vascular treatment fluid by contactlessly agitating a volume of the treatment fluid located in a barrel of a syringe; and injecting the foamed treatment fluid into a blood vessel of a patient with the syringe, contactlessly agitating can comprise moving an agitator member within the syringe. In such embodiments, moving the agitator member can comprise employing a contactless drive which is contactlessly coupled to the agitator member and located entirely outside the syringe. In such an embodiment, the contactless drive can comprise a magnetic drive which is magnetically coupled to the agitator member.

BRIEF DESCRIPTION OF THE DRAWINGS

FIGS. 3A and 3B illustrate a foaming element configured for linear foam generation;

FIGS. 4A, 4B, and 4C illustrate a foaming element configured for rotary foam generation;

DETAILED DESCRIPTION OF THE PREFERRED EMBODIMENTS

Although certain preferred embodiments and examples are disclosed below, it will be understood by those skilled in the art that the invention(s) disclosed herein extend beyond the specifically disclosed embodiments to other alternative embodiments and/or uses of the invention(s) and obvious modifications and equivalents thereof Thus, it is intended that the scope of the invention(s) herein disclosed should not be limited by the particular disclosed embodiments described below.

Embodiments are described herein using flow diagrams that have steps in a particular order, and the order of the steps in the flow diagrams is not to be considered to be limiting. Other methods with different orders of steps are also compatible with embodiments described herein. In addition, other methods with additional steps are also compatible with embodiments described herein.

As described further below, a sclerotherapy foam generator can include a magnetically driven impeller in a syringe barrel. A mixture of liquid and air can be drawn into the syringe. Foam can be created by moving the impeller inside the syringe barrel and causing a foaming liquid to flow through or around the impeller within the syringe barrel, which can thus act as a foaming chamber.

Figure 2:
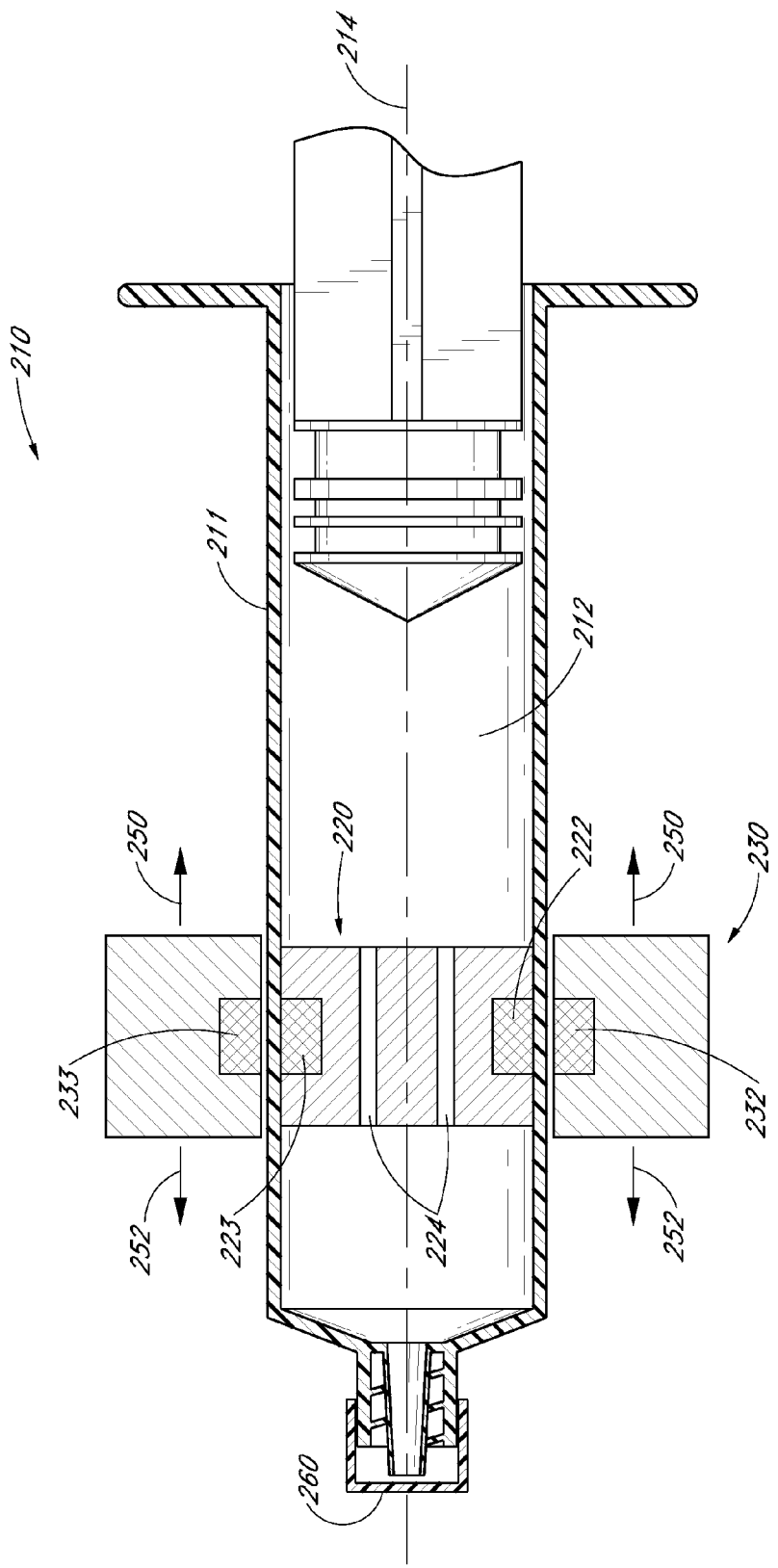
FIG. 2 is a cross-sectional view of a foam generation system having a syringe and a foaming element configured for linear movement.

One design of a sclerotherapy foam generator includes an axial, linear, or reciprocating impeller (or foaming element). A magnetically driven impeller is located inside the barrel of a disposable syringe. The impeller is fitted snugly with the syringe barrel and acts as the piston. The impeller has bores or fine openings through the impeller body to allow liquid and gas (e.g. air, $CO_2$) to pass through. Preferably, there are 1-5 holes having a diameter of 0.010 inch to 0.030 inch each. In one embodiment, there are 2 holes of 0.020 inch diameter. In another embodiment, more than 5 holes are employed with a hole diameter of less than 0.010 inch. Generally, decreasing hole diameter coincides with increasing hole count. A console for use with the syringe can advantageously comprise a linear actuator. For example, inside the console, a magnetic coupler can be mounted on a reciprocal motion system. When activated, the motion system can pull the impeller back and forth, via the magnetic coupler, for a predetermined cycle time. FIGS. 2, 3A, and 3B show embodiments of foaming systems or portions thereof, which can employ primarily or solely linear reciprocating movement of the impeller.

The magnetic coupler advantageously facilitates contactless driving and movement of the impeller within the syringe barrel. Such contactless driving and movement permits the vascular treatment fluid and the created foam to remain within the injection syringe and thus sterile for injection into a patient. Furthermore, contactless driving and movement facilitates injection of the foam very soon after preparation, minimizing the time available for the foam to decompose before injection.

Another embodiment of the impeller (or foaming element) is a radial, rotating impeller. The impeller, or bead, spins around its axis. Elongate protrusions in the form of, e.g., pin-like impeller elements can project from the impeller body. Or, the magnetic impeller can include a paddle impeller element, like a fin, with perforations or holes. Preferably, the holes have a diameter of 0.010 inch to 0.060 inch each. In one embodiment, there are 11 holes of 0.030 inch diameter. In another embodiment, more than 20 holes are employed with a hole diameter of less than 0.010 inch. Generally, decreasing hole diameter coincides with increasing hole count. The paddle may be a full-width paddle or a half-width paddle. The paddle creates turbulence and bubbles in the surrounding liquid(s) when it spins at a high speed. The console can advantageously comprise a rotary actuator. Such a rotary actuator can be advantageously employed with a foaming element (or impeller) that has a fin or is otherwise designed to spin. FIGS. 4A-4C, 5, 7, and 8 show embodiments of foaming systems or portions thereof, which can employ primarily or solely rotary movement of the impeller.

Figure 1:
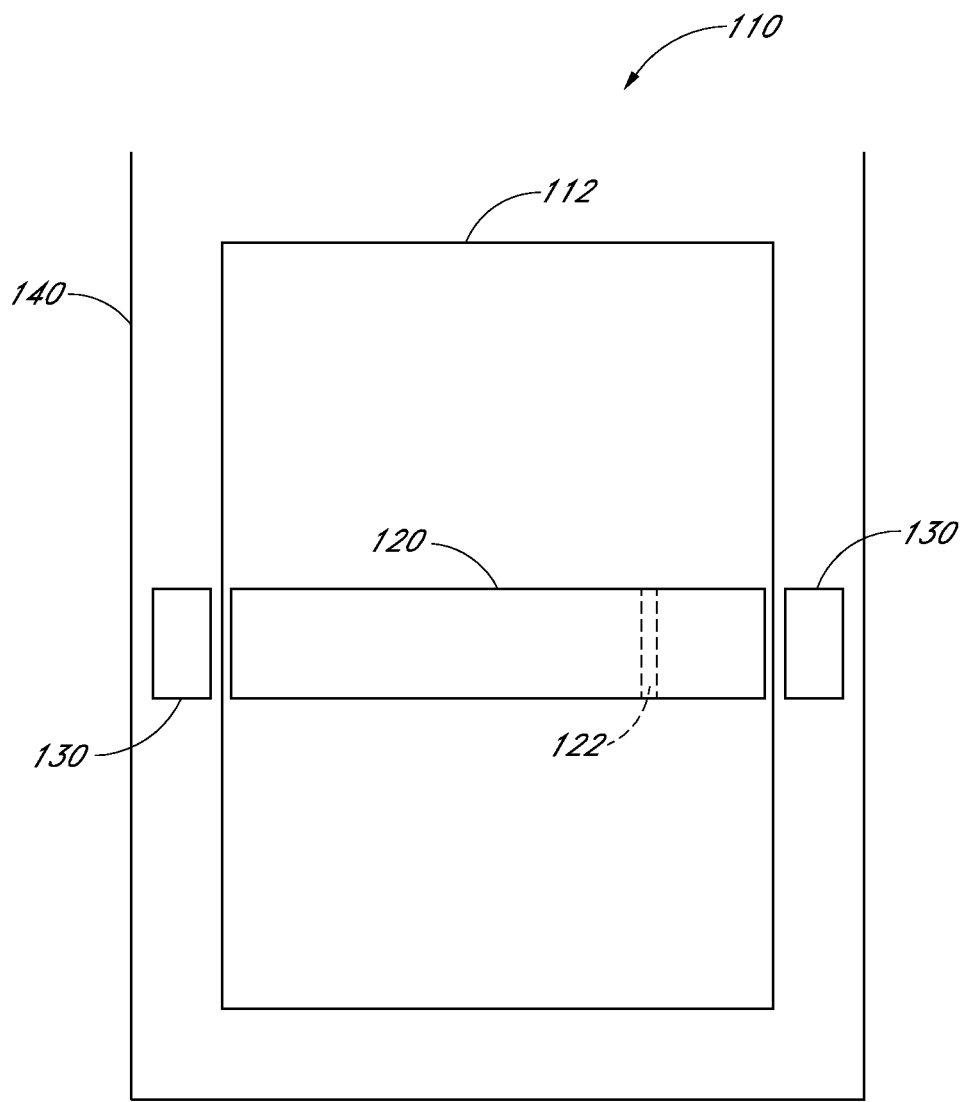
FIG. 1 is a schematic illustration of a foam generation system.

FIG. 1 schematically illustrates one embodiment of a foam generation system 110. The system can comprise a foaming chamber 112 that has a foaming element 120, that is advantageously disposed within the foaming chamber 112. The foaming element 120 is preferably movable within the foaming chamber 112, and to facilitate this movement in the presence of a flat liquid and/or foam, a flow passage 122 is preferably present within or adjacent to the foaming element 120. The foaming element 120 can act as an impeller, a piston, a linear actuator, and/or a rotary actuator. In some embodiments, the foaming chamber 112 can be an interior portion of a syringe, for example. In some embodiments, the foaming element 120 can be a plastic bead that is placed inside a disposable syringe. Preferably, the foaming element 120 is fitted snugly within the foaming chamber 112, which can be a syringe barrel. In some embodiments, the foaming element 120 comprises one or multiple magnets (not separately shown in FIG. 1).

The foam generation system 110 can also comprise a drive unit 130. In some preferred embodiments, the drive unit 130 can cause the foaming element 120 to move without touching the foaming element 120. For example, the drive unit 130 can employ a magnet, electromagnetic coil other device to exert a force over a distance without contacting the foaming element 120.

With further reference to FIG. 1, a base 140 can provide support and/or shelter for the drive unit 130. The base 140 can also have an opening into which the foaming chamber 112 can be removably inserted. Preferably, the drive unit 130 is positioned such that when the foaming chamber 112 is inserted into the base 140, the drive unit 130 is adjacent the foaming element 120 located within the foaming chamber 112. FIG. 1 illustrates how the drive unit 130 can be positioned in an adjacent fashion without contacting the foaming element 120. In some embodiments, the drive unit 130 can move in a reciprocating linear manner, causing the foaming element 120 to move up and down in the foaming chamber 112. In some embodiments, the drive unit 130 can move in a rotary manner, causing the foaming element 120 to rotate. In other embodiments, the drive unit 130 can remain stationary and be energized to create an electromagnetic field moving either linearly along or radially around the foaming chamber 112 to drive the foaming element 120.

In some embodiments, the foaming chamber 112 can contain, among other things, a fluid that can be a precursor to foam. Preferably, the fluid can be whipped into a foam through the agitation or other movement of the foaming element 120 within the foaming chamber 112. In some embodiments, the fluid occupies less volume before becoming foam than it does after becoming a foam. Thus, it can be advantageous to provide another fluid, such as a gas, inside the foaming chamber 112. The fluid precursor to foam can be infused with bubbles of the gas, creating the foam. In some embodiments, the fluid is a vascular treatment fluid that can be inserted into the vasculature (e.g., veins, arteries, or other anatomical passages) to have a desired treatment effect. In some embodiments, the vascular treatment fluid comprises a sclerosant.

FIG. 2 illustrates an embodiment of the more generalized foam generation system 110 illustrated in FIG. 1. The system 210 comprises a syringe 211 having a foaming chamber 212 within the syringe barrel. The foaming chamber also houses a foaming element 220 that acts as a magnetic linear actuator. The foaming element 220 comprises a magnet 222 and a magnet 223, the magnets disposed on either side of the foaming element 220 next to the sidewalls of the foaming chamber 212. The syringe 211 has a longitudinal axis 214, along which the foaming chamber 212 is aligned. The foaming element 220 comprises two flow passages 224 that are also aligned with the longitudinal axis 214.

The system 210 further comprises a drive unit 230 having a magnet 232 and a magnet 233. In a working configuration, the magnet 232 is preferably located adjacent to the magnet 222 located within the foaming element 220. Similarly, the magnet 233 is preferably located adjacent the magnet 223 when the drive unit 230 is functioning to move the foaming element 220. As indicated by the arrows 250 and 252, the drive unit 230 moves up and down in a direction parallel to the longitudinal axis 214 of the syringe 211. According to the magnetic interaction between the magnets 232, 222, 233, and 223, the foaming element 220 also moves within the foaming chamber 212 up and down in a direction parallel to the longitudinal axis 214.

Preferably, the foaming chamber 212 contains a treatment fluid, which can be a vascular treatment fluid, such as a sclerosant, and as the treatment fluid flows through the flow passages 224, the forces involved cause the treatment fluid to become a foam. The polarity of the magnets 233 and 232 can be aligned in the same direction as the magnets 223 and 222, or in a different direction. Thus, the drive unit 230 can be configured to attract the foaming element 220, or to repel the foaming element 220. The attractive or repulsive forces can be used to cause movement of the foaming element 220.

In some embodiments, a cap 260 is included to close off the end of the foaming chamber 212, preventing treatment fluid and/or foam from dripping or otherwise egressing from the tip of the syringe 211 during the foam generation process. The cap 260 preferably secures snugly to the tip of the syringe 211, for example, using a luer lock.

FIG. 3A illustrates an embodiment of a foaming element 310 that can be employed in place of the foaming element 220 of FIG. 2. The foaming element 310 comprises a body 312, a first end surface 314, and a second end surface 316. The foaming element 310 also comprises two flow passages 324, and openings 321 for receiving a magnet 322 and another magnet 323.

FIG. 3B shows a cross-sectional view of the foaming element 310 of FIG. 3A. In this view, the first end surface 314 is to the right, and the second end surface 316 is to the left. The longitudinal axis 330 is shown using a dashed line that runs horizontally through the foaming element 310. This cross-sectional view shows how one portion of the flow passage 324 can have a different diameter than another portion. For example, a larger diameter portion 332 is shown to the left, and a smaller diameter portion 334 is shown to the right. Having flow passages 324 with different diameters can provide more fluid turbulence when the foaming element 310 moves linearly back and forth along the longitudinal axis 330. More fluid turbulence can allow a more efficient foaming effect. The cross-sectional view of FIG. 3B also shows the opening 321.

FIG. 4A shows an end view of a foaming element 410 that can fulfill the function described above with respect to the foaming element 120 of FIG. 1. The foaming element 410 has a paddle 440 that extends across half the width of the foaming element 410. The foaming element 410 also has a body 412 and two side channels 424. The foaming element 410 is primarily intended for use as a rotary foaming element which functions by rotating the paddle 440 within the vascular treatment fluid in the foaming chamber. The side channels 424 advantageously facilitate injection of the created foam past the body 412 when the foam is complete.

FIG. 4B shows a side view of the foaming element 410. This view shows the channel 424 extending longitudinally along the body 412 of the foaming element 410. This view also shows the paddle 440 extending from the end of the foaming element 410, and it also shows the holes 442 in the paddle 440. The foaming element 410 has a longitudinal axis 430.

FIG. 4C shows an exploded, elevational view of the foaming element 410. The paddle 440 is shown extending from one side of the body 412. The magnet 422 is shown separately from the body 412, but as indicated, an opening 423 can be sized to receive the magnet 422. The channel 424 is also shown in the body 412 of the foaming unit 410.

The foaming unit 410 is configured to produce foam from rotary movement. One example of rotary movement is spinning movement about a longitudinal axis 430. The liquid can be turned into foam as the body 412 spins around its own longitudinal axis 430, causing liquid to quickly flow through the holes 442 in the paddles 440. Additionally, fluid can flow through the channels 424 if the body 412 moves along the longitudinal axis 430. Thus, in some embodiments, both linear and rotary movements can occur. Again, the side channels 424 also provide for flow of the foam past the body 412 during injection.

The foaming element 410 shown in FIGS. 4A-4C is different from the foaming element 310 shown in FIGS. 3A-3B for the additional reason that the foaming element 410 does not comprise two side magnets, but instead includes a single magnet 422. The magnet 422 advantageously has a positive pole and a negative pole, and thus any corresponding magnets in an external drive unit would preferably be oriented appropriately to correspond to those poles. Thus, the drive unit used for the foaming element 410 differs from the drive unit 130 in at least two ways. The two drive units are preferably configured to move differently, but their orientations can also be different to accommodate a single magnet versus two separate magnets. However, in some embodiments, the drive unit can move in a similar fashion for both the foaming element 410 and the foaming element 310, even if the magnets themselves are configured differently.

A linear foam generation method can comprise, in various embodiments, any or all of the following steps: 1) drawing a small amount of sclerosing solution into a syringe; 2) pulling back the syringe plunger to draw more air (or other gas(es) such as carbon dioxide or nitrous oxide); 3) placing a cap at the tip of the syringe; 4) inserting the syringe into a foam generator; 5) activating a set of magnetic couplers mounted on the reciprocal motion system (e.g., automatically, using a photosensor); and/or 6) allowing the magnetic couplers to move a foaming element back and forth, forcing liquid and air through holes in the foaming element. Where the magnetic coupler is a static electromagnetic stator, step (5) above can comprise instead sequentially energizing segments of an electromagnetic coil or coil array at high speed and in an linear, reciprocating progression along the longitudinal axis of the syringe to linearly reciprocate the foaming element within the syringe.

Figure 5:
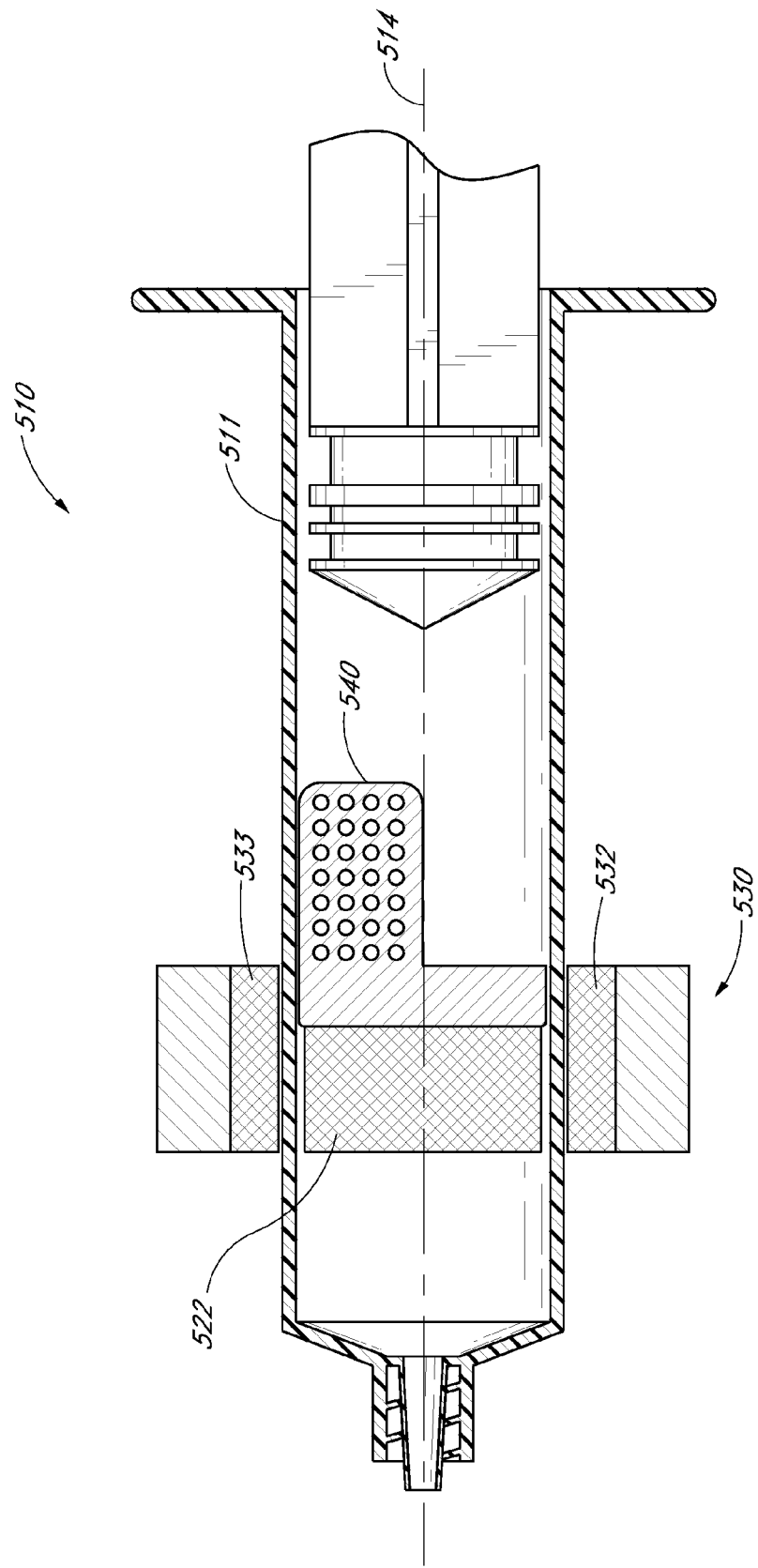
FIG. 5 is a cross-sectional view of a foam generation system having a syringe and a foaming element configured for rotary movement.

FIG. 5 illustrates a system 510 that can incorporate a foaming element such as the one described in FIGS. 4A-4C. The foaming element has a paddle 540 and a magnet 522, and the system 510 is depicted in cross-section. A drive unit 530 is located outside a syringe 511, but the magnets 532 and 533 and the drive unit 530 are located adjacent the magnet 522 in the foaming element. The magnet 532 attracts one pole of the magnet 522 and the magnet 533 attracts the other pole of the magnet 522. The drive unit 530 can spin around the syringe 511 such that rotation occurs about the longitudinal axis 514 of the syringe 511. Thus, the paddle 540 spins within the chamber of the syringe 511, causing fluid to flow through the holes in the paddle, and creating foam.

A rotary foam generation method can comprise any or all of the following steps: 1) drawing a small amount of sclerosing solution into a syringe; 2) pulling back the syringe plunger to draw more air (or other gas(es) such as carbon dioxide or nitrous oxide); 3) placing a cap at the tip of the syringe; 4) inserting the syringe into a foam generator; 5) activating a rotary actuator and a magnetic coupler (e.g., using an electronic circuit for sensing that the syringe is in place); 6) allowing the magnetic coupler to spin around the syringe at high speed; 7) using the magnetic coupler to cause a foaming element to spin within the syringe; 8) forcing liquid and air through holes in the foaming element; and/or 9) using a timer to determine when to stop rotation. Where the magnetic coupler is a static electromagnetic stator, step (6) above can comprise instead sequentially energizing quadrants or circumferential segments of an electromagnetic coil or coil array at high speed and in an angular progression around the longitudinal axis of the syringe to rotate the foaming element within the syringe.

In some embodiments, the sclerotherapy foam generator includes a magnetic drive console or box. One embodiment of the box has a rotating magnetic drive field, which rotates the impeller in the foaming chamber. This embodiment of the box includes physically rotating magnets and/or sequentially activated coils in a circular stator. Another embodiment of the box has a reciprocating magnetic drive field, which moves the impeller linearly. This embodiment of the box has physically rotating magnets and/or sequentially activated coils in a linear stator. One design of the magnetic drive box has a source of foaming gas on board. The gas can be $CO_2$ or $N_2O$, for example.

Figure 6:
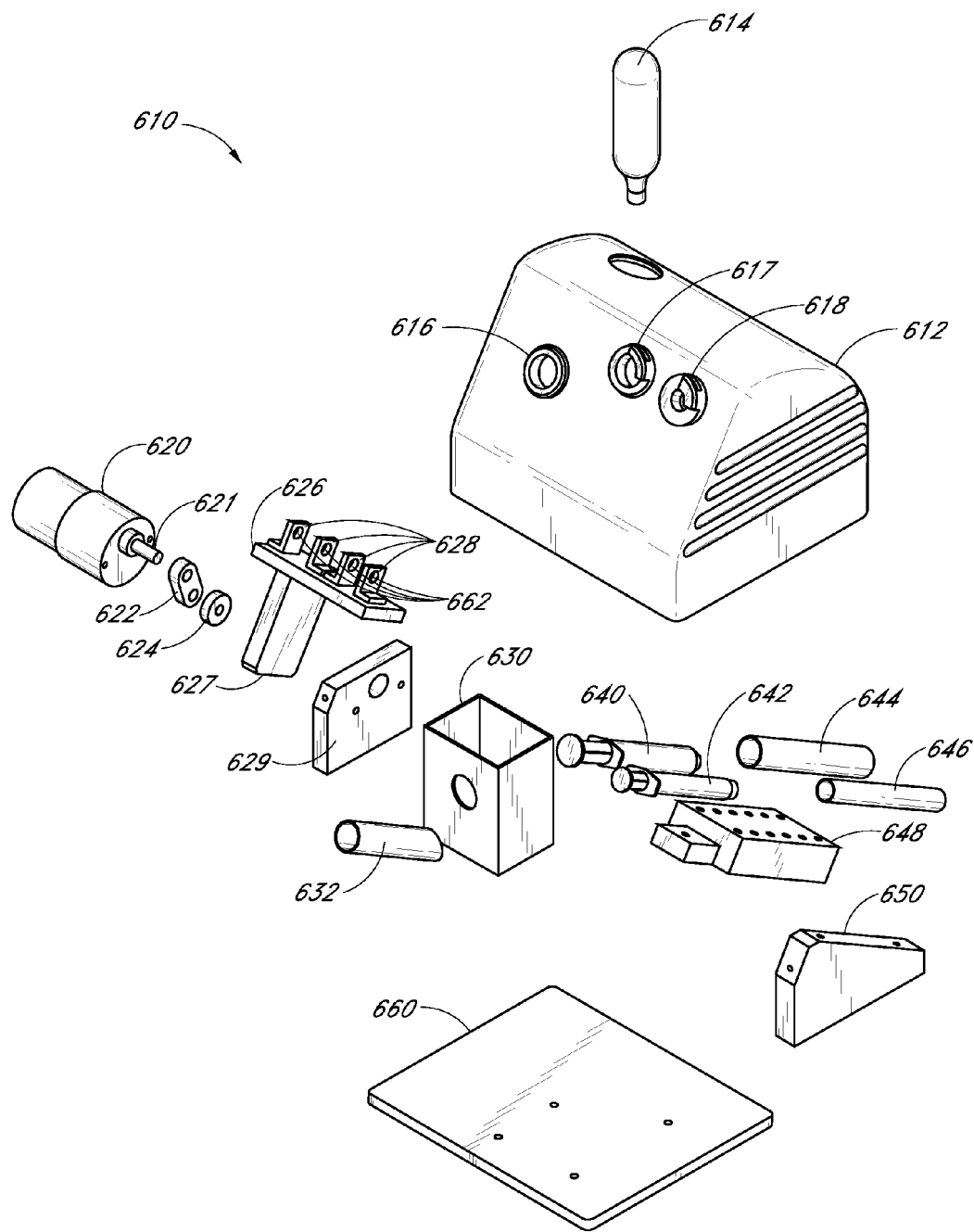
FIG. 6 illustrates the components of a foam generation system.

FIG. 6 illustrates another embodiment of a foam generation system 610. The system 610 can comprise a drive console 612 with a contactless drive system and, in the depicted embodiment, a gas delivery system as well. The depicted gas delivery system includes an opening in the console 612 to receive a gas canister 614. The gas canister 614 can contain carbon dioxide, for example. Other gases can also be contained, such as nitrous oxide, air, and/or nitrogen. The gas delivery system can further comprise a gas chamber 630 in fluid communication with the gas canister 614 and its corresponding opening, so that the gas chamber 630 can receive gas from the canister 614. A syringe support 632 is in communication with the gas chamber 630 and facilitates insertion of a syringe into the gas chamber 630 to receive gas from the canister 614. An opening 616 in the console 612 permits insertion of a syringe into the support 632. An optional luer fitting can be incorporated in the syringe support 632 to facilitate connection of a syringe to the canister 614 or the gas chamber 630. Such a luer fitting may be useful for adding lighter-than-air gases to the syringe which, contrary to heavier-than-air carbon dioxide, will not tend to settle to the bottom of the gas chamber 630.

The contactless drive system of the console 612 can comprise magnet brackets 628 which are mounted for reciprocating movement relative to one or more syringes 640, 642 disposed in corresponding syringe supports 644, 646. The magnet brackets 628 are mounted on a track support 626 and track 627, which are moveable on and along a slide 648. The slide 648 is fixed to a base plate 660 via a slide mount 650. The syringe supports 644, 646 are located above the slide mount 650, and the magnet brackets 628 and track support 626 are positioned such that the supports 644, 646 are received between respective pairs of the magnet brackets. The magnet brackets 628 thus hold a magnet 662 on each side of the syringe supports 644, 646.

The magnet brackets 628, the magnets held thereby, the track support, etc. are moveable back and forth on the slide 648 via a motor 620 with a crankshaft 621. The crankshaft 621 can connect to a crank arm 622, which in turn connects to a cam follower bearing 624 and the track 627. A motor mount 629 is depicted for securing the motor 620 to the base plate 660.

The console 612 can accommodate a large syringe 640 (e.g., a 5 cc syringe) and/or a small syringe 642 (e.g., a 3 cc syringe). The large syringe can be inserted into the large syringe support 644, and the small syringe 642 can be inserted into the small syringe support 646. Clips are depicted at the openings 617, 618 of the supports 644, 646 and are usable to hold the flanges of the syringes and prevent movement of the syringes within the supports 644, 646 during use.

The depicted embodiment of the console 612 thus facilitates a linear contactless magnetic drive system which moves magnets within the magnet brackets 628 relative to one or more syringes 642, 644 disposed within the supports 644, 646. Any of the "linear" foaming elements disclosed herein can be employed in the syringes 642, 644 to create a foaming action in the syringe barrels in response to movement of the magnets. The gas delivery system, as described above, can be used first to add a desired amount of gas to vascular treatment liquid in the syringe(s) before the syringe(s) are processed by the contactless drive system.

In variations of the console 612, the depicted moving-magnet drive system can be replaced with a static or solid state contactless magnetic drive comprising a static linear arrangement of electromagnets (e.g. coils) which can be activated sequentially to create a magnetic field that reciprocates linearly along the syringe support(s) 644, 646. A moving-magnet or static rotary contactless magnetic drive can be employed in still other embodiments. As another alternative, a contactless electrostatic drive can be employed which includes a drive system that generates a reciprocating electric field to move electrically-charged impeller(s) within the syringe(s). Such an electrostatic system can be embodied in a motorized moving system as depicted in FIG. 6, or in a solid state system as described above. As still another alternative, a contactless inertial drive system can be employed in the console 612, comprising a mechanical linear shaker which shakes the syringe(s) in a linear, longitudinal back and forth fashion to move the impeller(s) back and forth longitudinally within the syringe barrels. Finally, it should be further noted that any of the contactless drive systems described herein as suitable for the console 612 can be employed as a drive system in any of the embodiments of the foam generation system disclosed herein.

Figure 7:
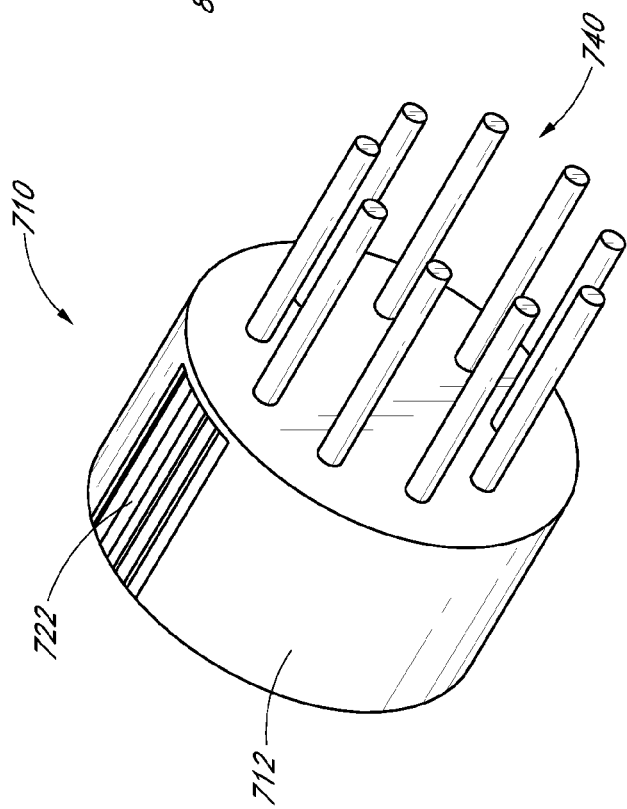
FIG. 7 illustrates a foaming element having elongate protrusions.

FIG. 7 illustrates an alternative foaming element 710 which can be employed in the various embodiments of the foam generation system disclosed herein. This foaming element 710 has a body 712 and a magnet 722. The foaming element 710 also has elongate protrusions 740. The elongate protrusions 740 can each have the general shape of a pin. For example, as illustrated, the elongate protrusions 740 can extend from the body 712 of the foaming element 710. The elongate protrusions 740 can be arranged generally in a circle pattern where adjacent elongate protrusions 740 in the circle are spaced equidistantly apart. Alternatively, elongate protrusions could be scattered randomly across the body 712, or have any other configuration that may be advantageous for stirring foam. The foaming element 710 can be moved in a rotary motion, causing a vortex within a foaming chamber, and the elongate protrusions 740 can serve as small paddles to facilitate making foam in the foaming chamber.

Figure 8:
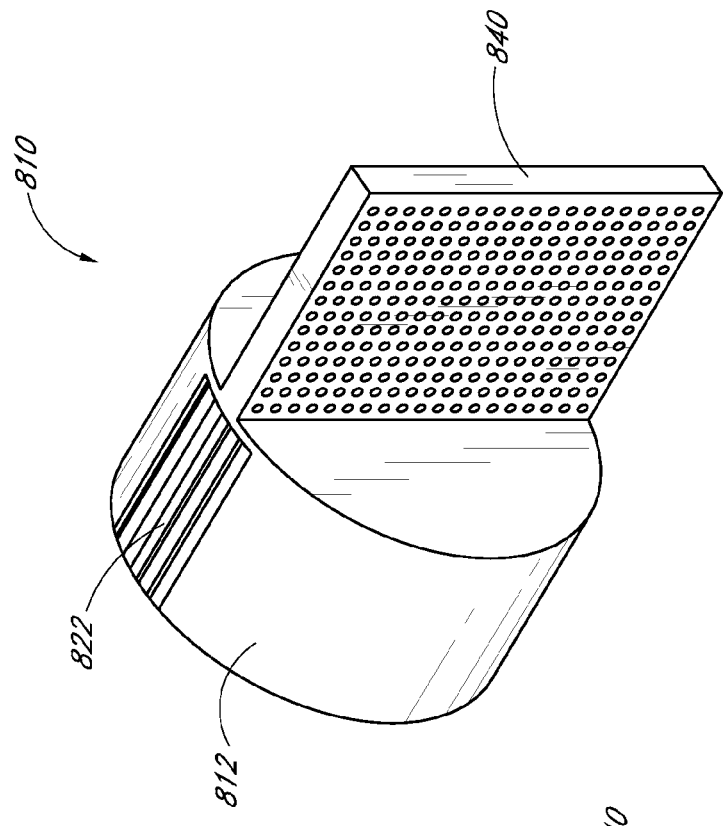
FIG. 8 illustrates a foaming element having a paddle with holes.

FIG. 8 shows an alternative embodiment of a paddle-type foaming element 810 which can be employed in the various embodiments of the foam generation system disclosed herein. The foaming element 810 can have a paddle 840 that extends across the entire width of the foaming element 810, in contrast to the partial-width or half-width paddle of FIGS. 4A-5. The foaming element 810 has a body 812 and a magnet 822. The foaming element 810 can otherwise be constructed and function in generally the same manner as that described for the foaming element 410 of FIGS. 4A-4C.

Figure 9:
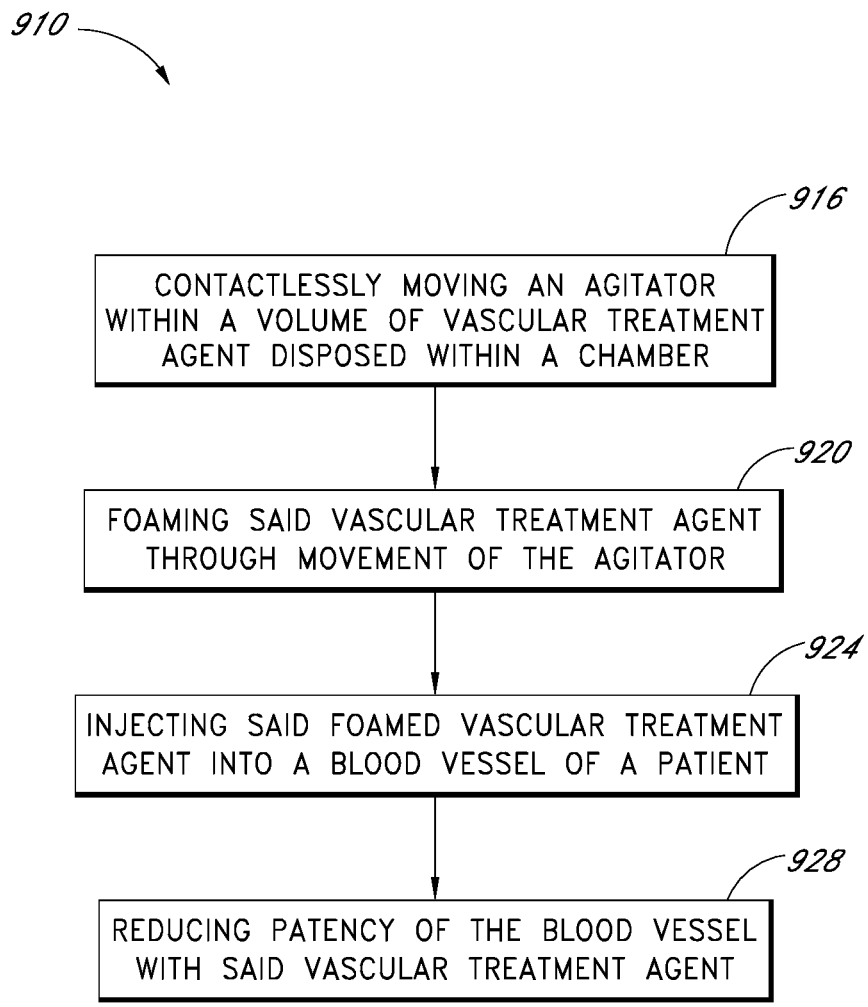
FIG. 9 illustrates four steps of a method of foam generation.

FIG. 9 schematically illustrates one embodiment of a method 910 of preparing vascular treatment agent. The method 910 can comprise contactlessly moving an agitator (such as a foaming element or impeller, for example) within a volume of vascular treatment agent disposed within a chamber, as set forth at 916. The movement of the agitator can cause the vascular treatment agent to become foam. In some embodiments, the foaming effect is caused or enhanced by the introduction of gas (e.g., in the form of bubbles) into the vascular treatment agent. A further step can comprise foaming the vascular treatment agent through movement of the agitator, as illustrated at 920.

A further step can comprise injecting said foamed vascular treatment agent into a blood vessel of a patient, as illustrated at 924. In some embodiments, the agent can comprise a sclerosant. In some embodiments, the blood vessel can comprise a vein. Advantageously, the vascular treatment agent can be used to reduce the patency of the blood vessel, as shown at 928.

In the method 910, and in other methods as well, movement of the agitator can be accomplished in various ways. Two advantageous types of movement are linear and rotary. For example, where a foaming chamber has a longitudinal axis (and preferably where the foaming chamber has a generally consistent cross-section along that axis), the agitator can be moved by linearly reciprocating the agitator along said longitudinal axis. In some embodiments, however, especially those with a certain amount of cylindrical symmetry, the agitator can rotated. For example, where the foaming chamber has a longitudinal axis, the agitator can be rotated about said longitudinal axis.

The force causing movement of the agitator is advantageously a non-contact force, such as an electromagnetic, electrostatic or inertial force. In some embodiments, the method of contactlessly moving the agitator can comprise magnetically moving the agitator. Thus, the agitator can be magnetically coupled to a magnetic drive unit. The magnetic drive unit can be located in a piggy-back manner on the side of a syringe, for example. Alternatively, the magnetic drive unit can receive the syringe (as illustrated in FIG. 6). The drive unit can contactlessly move the agitator within the syringe.

In some embodiments of the method 910 and other methods, contactlessly moving the agitator can comprise electrostatically moving said agitator. Alternatively, contactlessly moving the agitator can comprise inertially moving said agitator, such as by manually shaking the foaming chamber or employing a mechanical shaker to shake the foaming chamber.

In some embodiments of the method 910 and other methods, the agitator can comprise a member having one or more flow passages therein, such as the foaming elements 120, 220, 310, 410, and 810. Preferably, moving the agitator comprises forcing at least a portion of a vascular treatment agent through one or more of these flow passages.

Figure 10:
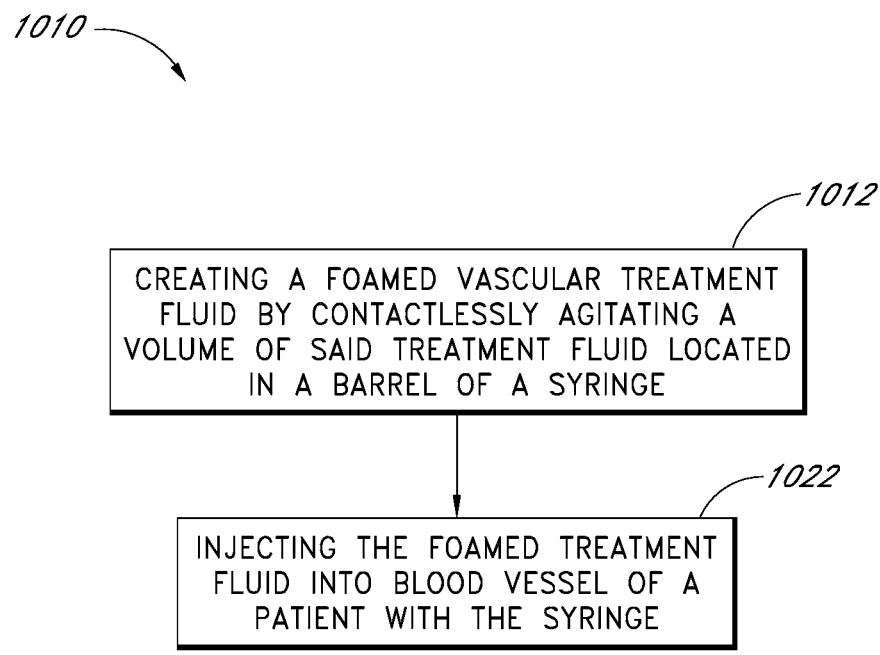
FIG. 10 illustrates two steps of a method of foam generation.

FIG. 10 shows a method 1010 of vascular therapy comprising 1) creating a foamed vascular treatment fluid by contactlessly agitating a volume of said treatment fluid located in a barrel of a syringe, as shown at 1012; and 2) injecting the foamed treatment fluid into a blood vessel of a patient with the syringe, as shown at 1022. The method 1010 of vascular therapy can be used with a treatment fluid comprising a sclerosant, and the blood vessel can comprise a vein. In some embodiments, the vein is a varicose vein. In some embodiments, contactlessly agitating comprises contactlessly moving an agitator member within said syringe. The method 1010 can further comprise employing a contactless drive which is contactlessly coupled to the agitator member and located entirely outside the syringe. Moreover, the contactless drive can comprise a magnetic drive that is magnetically coupled to the agitator member. In further variations, any of the contactless drive systems or methods of contactless movement disclosed herein can be employed.

Figure 11:
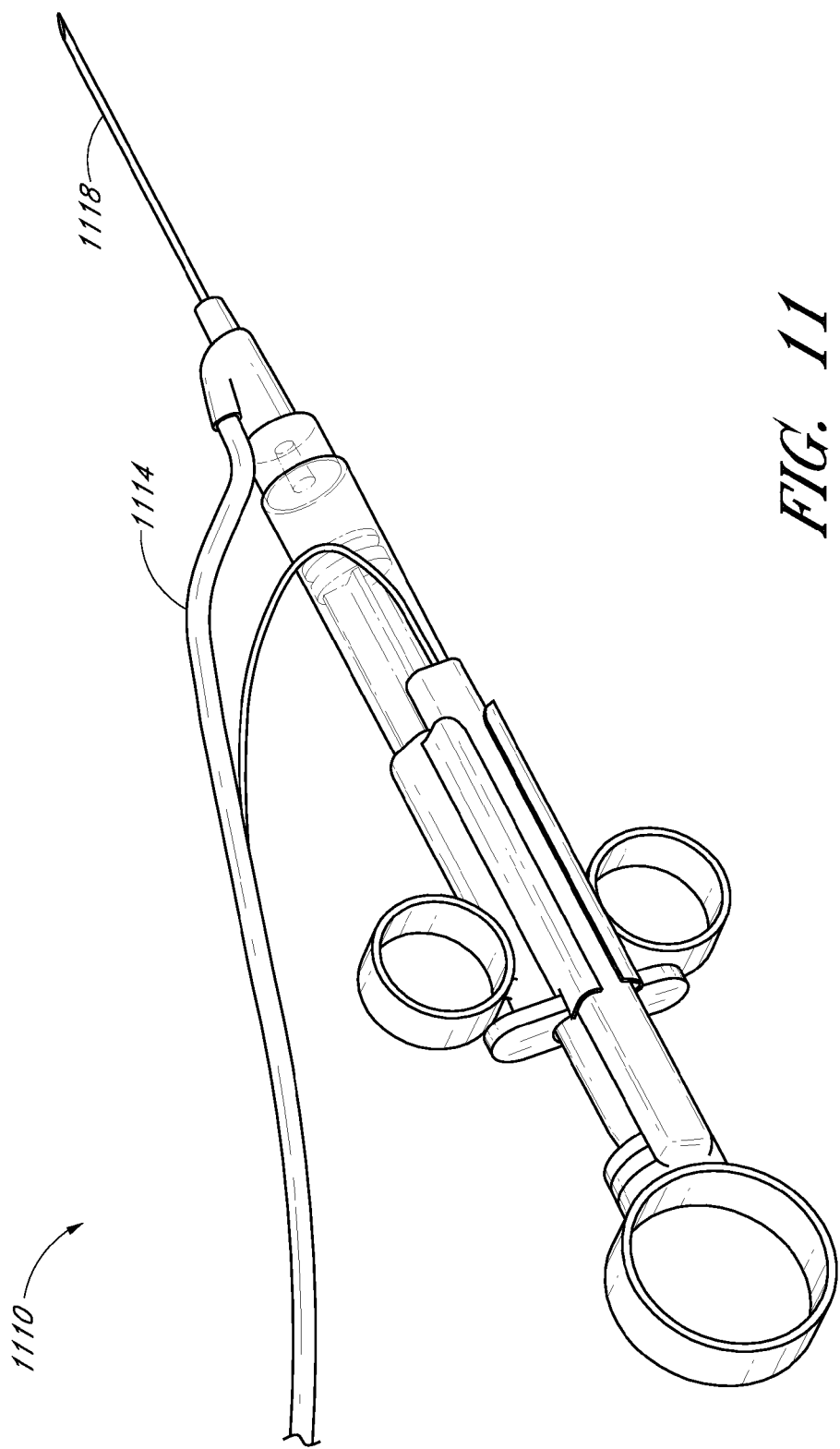
FIG. 11 illustrates a needle-tip gas mixer.

With reference to FIG. 11, some embodiments of the foam generation system comprise a needle-tip gas mixer 1110. A gas tube 1114 can provide a flow of gas toward the syringe needle 1118. A gas injector can extend coaxially into the syringe needle. The gas injector tip can have a shape, e.g. a "duckbill" shape, selected to enhance gas injection efficacy. Instead of or in addition to such a tip shape, the gas injector barrel can have micro-perforations in its sidewalls and/or tip to facilitate passage of gas from the injector to surrounding liquid. The gas injected into the needle 1118 can be $CO_2$, air, $N_2O$, or nitrogen, for example. The gas can be introduced together with the sclerosing agent or other liquid to be mixed at or near the tip of the needle 1118 or catheter. The gas is mixed with the sclerosing agent at the point of use and creates a foam that is delivered to the vessel to be sclerosed. The needle tip gas mixer 1110 comprises a needle 1118 that can include a center tube for introducing the mixing gas. Additionally, the needle tip gas mixer 1110 can comprise a syringe with a pressure sensitive switch that activates the gas flow as the syringe plunger is depressed to inject the sclerosant. The two fluids mix together at or near the tip of the needle or catheter to form a foam mixture of the two fluids before exiting the needle.

Some embodiments for generating sclerotherapy foam comprise a device, such as a syringe, with an in-line magnetic or other contactless impeller chamber with an on board motor. Such a device can include a foaming chamber, an impeller with a magnetic or other contactless coupler, and a motor that is positioned on the side of the foaming chamber to contactlessly drive the impeller within the chamber. Thus a complete foam generation system is facilitated in a single hand-held unit.

Various embodiments of the present invention(s) have been described above. Although the invention(s) have been described with reference to these specific embodiments, the descriptions are intended to be illustrative of the invention(s) and are not intended to be limiting. Various modifications and applications may occur to those skilled in the art without departing from the true spirit and scope of the invention(s) as defined in the appended claims.

What is claimed is:

1. Apparatus for preparing foamed vascular treatment fluid, said apparatus comprising:
   a foaming chamber;
   a vascular treatment fluid in said chamber;
   a foaming element in said chamber, said foaming element being moveable within said chamber and in said fluid;
   said foaming element having one or more flow passages therein so that movement of said foaming element in said vascular treatment fluid tends to force said fluid through said one or more flow passages; and
   a drive unit located outside said chamber, said drive unit being configured to drivingly couple to said foaming element without a drive shaft or other linkage extending into said chamber.

2. The apparatus of claim 1, wherein said chamber comprises a syringe barrel.

3. The apparatus of claim 1, wherein said drive unit is configured to magnetically couple to said foaming element.

4. The apparatus of claim 1, wherein said drive unit is configured to electrostatically couple to said foaming element.

5. The apparatus of claim 1, wherein said vascular treatment fluid comprises a sclerosant.

6. The apparatus of claim 1, wherein:
   said foaming element is magnetic;
   said drive unit further comprises a magnetic drive unit configured to magnetically engage said foaming element.

7. The apparatus of claim 6, wherein said magnetic drive unit is housed in a base which is configured to removably receive said foaming chamber.

8. The apparatus of claim 7, wherein said chamber is located in a syringe and said base forms a receptacle which is configured to removably receive said syringe.

9. The apparatus of claim 8, wherein said magnetic drive unit is configured to magnetically engage said foaming element upon placement of said syringe in said receptacle.

10. Apparatus for preparing a vascular treatment agent, said apparatus comprising:
    a syringe, said syringe having an internal chamber containing a vascular treatment fluid;
    an impeller located in said chamber;
    a drive system located entirely outside said chamber, said drive system being contactlessly and drivingly coupled to said impeller;
    said impeller comprising a generally solid member having one or more fluid flow passages extending therethrough, such that movement of said impeller in said treatment fluid tends to force said treatment fluid through said fluid flow passages.

11. The apparatus of claim 10, wherein said drive system is magnetically coupled to said impeller.

12. The apparatus of claim 11, wherein said impeller comprises a magnet and said drive system comprises a magnetic drive.

13. The apparatus of claim 10, wherein said vascular treatment fluid comprises a sclerosant.

14. The apparatus of claim 10, wherein said fluid flow passages have at least a portion with a diameter of 0.010 inch to 0.060 inch.

15. The apparatus of claim 10, wherein said drive system is housed in a base which is configured to removably receive said syringe.

* * * * *